United States Patent [19]

Levy

[11] 4,429,421

[45] Feb. 7, 1984

[54] METHOD OF IMPLANTING AN INTRAOCULAR LENS

[76] Inventor: Chauncey F. Levy, 1 Surrey La., Pittsford, N.Y. 14534

[21] Appl. No.: 345,330

[22] Filed: Feb. 3, 1982

[51] Int. Cl.³ .......................... A61F 1/16; A61F 9/00; A61B 17/00
[52] U.S. Cl. .................................... 3/13; 128/303 R; 128/303.1
[58] Field of Search ...................... 3/1, 13; 128/303.1, 128/303 R, 1 R

[56] References Cited

U.S. PATENT DOCUMENTS 4,190,049  2/1980  Hager et al. .................... 128/303 R
4,198,980  4/1980  Clark .............................. 128/303 R

OTHER PUBLICATIONS

"The Evolution of the Anterior Chamber Implant Up to, and Including the Choyce Mark IX", by D . P. Choyce, Ophth., vol. 86, Feb. 1979, pp. 197–206.
"Director for the Choyce Implant", by J. R. Kirickhoff, Reprint from American Journal of Ophthalmology, vol. 87, No. 4, Apr. 1979, pp. 569–570.

Primary Examiner—Ronald L. Frinks
Attorney, Agent, or Firm—Hoffman Stone

[57] ABSTRACT

Method of implanting an intraocular lens comprising the step of transilluminating the lens as it is introduced into the eye. In the preferred form two sources of light are used, complementary in color so that the edges of the lens glow white while it is properly aligned, and show color when it is moved out of alignment.

5 Claims, 3 Drawing Figures

METHOD OF IMPLANTING AN INTRAOCULAR LENS

BRIEF DESCRIPTION

This invention relates to a novel method of implanting an intraocular lens using the principle of transillumination to facilitate proper placement of the lens.

In lens implantation it is important that the lens be properly placed, and that during its introduction into the eye great care be taken not to damage the iris, which is a delicate structure. In the usual implantation procedure an arcuate incision is made along the edge of the cornea, the natural lens is removed, and the implantable lens is introduced through the incision, being moved in a plane generally normal to the main optical axis of the eye while the surgeon observes through a microscope aligned generally with the axis. The lens is moved across the surgeon's field of view, and it is often difficult to keep the lens always normal to the optical axis and to avoid moving it out of the desired plane. Also, partly because of the limited depth of field of the microscope and because of intervening tissue, the surgeon can easily lose sight of the lens during the procedure.

In accordance with the invention the problem is largely overcome by use of trans-, or edge illumination. Light is directed into the lens through an edge and in a plane parallel to the major plane of the lens so that it becomes illuminated around all its edges. All of its edges glow and the surgeon is enabled to keep track of the lens regardless of its position in the eye, even behind the iris, for example.

In accordance with an alternative, and presently preferred embodiment of the invention applicable primarily to implantation in the anterior chamber, two light sources are used playing in opposite directions. The sources are of complementary colors, and balanced for intensity, so that so long as the lens is kept in the desired plane its edges glow with white light. If the lens is tilted, or otherwise displaced out of the proper plane, colored light appears, indicating also the nature of the undesired displacement. One of the sources is applied to the lens through a light guide, or pipe, having its output face directly in contact with the lens. The other source is arranged to project a relatively thin sheet of light across the anterior chamber of the eye to define the desired plane.

DETAILED DESCRIPTION

Representative embodiments of the invention will now be described in detail in conjunction with the drawing, wherein.

Figure 1:
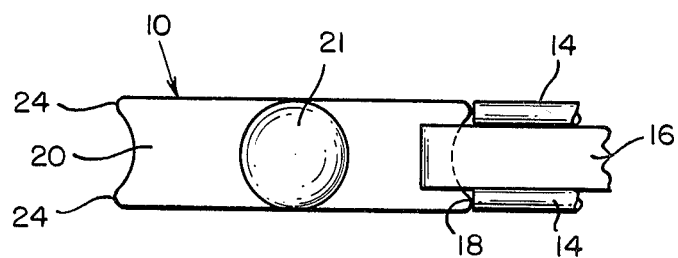
FIG. 1 is a fragmentary plan view of an intraocular lens held by a forceps and transilluminated in preparation for insertion into an eye.
Figure 2:
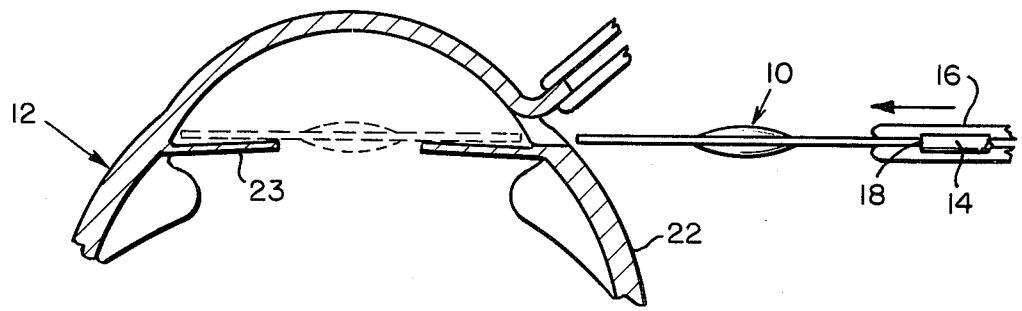
FIG. 2 is a fragmentary, cross-sectional view of an eye illustrating the implantation of a lens with edge lighting.

Referring now to FIGS. 1 and 2, in its simplest form the invention contemplates edge illumination of an intraocular lens 1 during its insertion into the eye 12. The procedure is effective for implantation in the posterior as well as the anterior chamber.

Most conveniently, a pair of light guides 14 are mounted on the forceps 16 used by the surgeon to hold the lens and are positioned thereon with their output faces 18 touching the proximal edge of the lens 10. Light from the guides 14 causes the edges of the lens 10 to glow, but not the major faces of the lens. It thus enables the surgeon to see the lens 10 in outline throughout the procedure even if it is passed through and brought behind the iris for implantation in the posterior chamber.

(The term lens herein is meant to denote the entire structure to be implanted including the haptic 20 as well as the refractive portion 21.)

The guides 14 may be of any desired form such as, for example, arrays of optical fibers, or solid rods of a transparent plastic. Their output faces 18 are shaped to conform to the edge portions of the lens touched by them, and to be slightly thinner than the lens so that light from the guides does not illuminate the major surfaces of the lens.

In the procedure illustrated the lens 10 is implanted in the anterior chamber and is not sutured in place but is merely trapped diametrically across the sclera 22 immediately in front of the iris 23. The invention also facilitates this procedure in that when the distal feet 24 of the haptic 20 come into contact with the sclera, light from the feet shines through the sclera and the surgeon sees glow points on the sclera clearly indicating the precise position of each of the feet 24.

Figure 3:
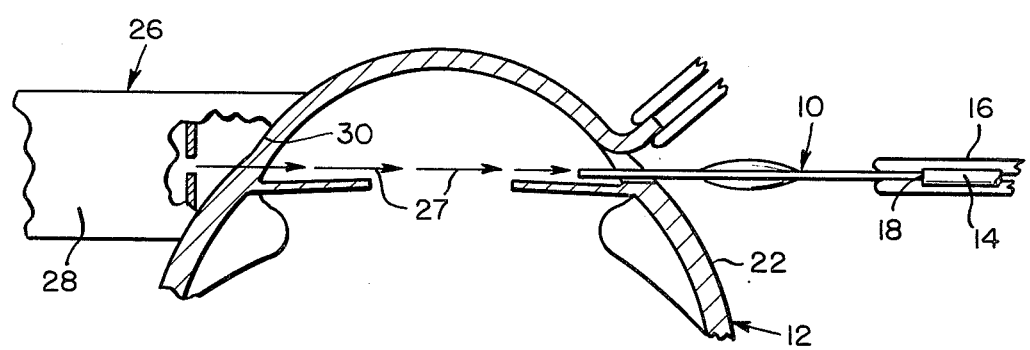
FIG. 3 is a fragmentary, cross-sectional view of an eye illustrating the implantation of a lens using double edge lighting with complementary colors.

In the presently preferred embodiment of the invention, which is presently thought to be useful principally for implantation in the anterior chamber, as shown in FIG. 3, a second light source 26 is used in addition to the guides 14. Colored light is used, mutually complementary, and balanced so that when seen together their sum is white, or reasonably close to white. The second source 26 is placed against the eye diametrically opposite from the incision through which the lens 10 is introduced. The second source 26 is designed to emit a relatively thin sheet of light (indicated by the arrows 27) in the plane in which the surgeon wants to move the lens 10 and finally place it.

In use, the surgeon sees the lens 10 edge illuminated with apparently white light so long as the lens is in the desired plane defined by the second source. Light from the two sources, illuminating the lens from opposite directions, is blended in the lens and is seen along the edges of the lens as white light. Any departure from the desired plane brings color to the edges, principally the color of the light from the guides 14.

In practice the second light source 26 is preferrably mounted in a substantial case 28, and its output face 30 is shaped as closely as possible to conform to the curvature of the eye. It is placed in contact with the eye and serves to restrain it against motion.

What is claimed is:

1. Method of implanting an intraocular lens or the like in an eye comprising the steps of making an incision in the eye to admit the lens, directing light into the lens through an edge thereof thereby to cause the edges of the lens to glow, and inserting the lens through the incision into the interior of an eye chamber while continuing to direct light into the lens.

2. Method according to claim 1 wherein the light is of a preselected color, and including the further step of directing a thin sheet of light of a color complementary to said preselected color through the anterior chamber of the eye in a selected plane generally normal to the central optical axis of the eye, whereby when the lens is in the selected plane its edges glow white and when the lens is displaced from the selected plane its edges become colored.

3. Method according to claim 2 wherein said thin sheet of light is emitted from a source having an output face that conforms generally to the curvature of the eye, and supporting said source sufficiently rigidly with its output face against the eye so that it serves to stabilize the eye against motion.

4. Method according to claim 1 wherein light is directed into the lens through a light pipe supported on the forceps used to hold the lens, and the output face of the light pipe is held in contact with an edge portion of the lens.

5. Method according to claim 2 wherein the light of complementary color is directed into the eye in a direction opposite from the direction of the light of said preselected color.

* * * * *